US008614185B2

(12) United States Patent
Heavner

(10) Patent No.: US 8,614,185 B2
(45) Date of Patent: Dec. 24, 2013

(54) FUSION PROTEINS OF ALPHA-MSH DERIVATIVES AND FC

(75) Inventor: George Heavner, Radnor, PA (US)

(73) Assignee: Centocor Ortho Biotech Inc., Horsham, PA (US)

(*) Notice: Subject to any disclaimer, the term of this patent is extended or adjusted under 35 U.S.C. 154(b) by 71 days.

(21) Appl. No.: 12/768,093

(22) Filed: Apr. 27, 2010

(65) Prior Publication Data

US 2010/0278845 A1   Nov. 4, 2010

Related U.S. Application Data

(60) Provisional application No. 61/175,921, filed on May 6, 2009, provisional application No. 61/176,294, filed on May 7, 2009.

(51) Int. Cl.
*A61K 38/00* (2006.01)
*A61K 39/395* (2006.01)

(52) U.S. Cl.
USPC ..... 514/10.7; 514/21.2; 424/178.1; 424/179.1

(58) Field of Classification Search
None
See application file for complete search history.

(56) References Cited

U.S. PATENT DOCUMENTS

| 5,635,603 A * | 6/1997 | Hansen et al. ............. 530/391.5 |
| 6,006,753 A | 12/1999 | Efendic |
| 2003/0211078 A1 | 11/2003 | Heavner |
| 2006/0105951 A1* | 5/2006 | Cunningham et al. .......... 514/12 |
| 2007/0015257 A1 | 1/2007 | Hedley et al. |
| 2008/0031848 A1 | 2/2008 | Konradi et al. |

FOREIGN PATENT DOCUMENTS

| WO | WO 98/08531 A1 | 3/1998 |
| WO | WO 98/19698 A1 | 5/1998 |
| WO | WO 99/64060 A1 | 12/1999 |
| WO | WO 00/16797 A2 | 3/2000 |
| WO | WO 00/07617 A1 | 12/2000 |
| WO | WO 2006/073772 A2 | 7/2006 |

OTHER PUBLICATIONS

Kolchanov, 1988, Journal of Molecular Evolution, vol. 27, pp. 154-162.*
Pasquo, 2012, PLoS ONE, vol. 7, Issue 2, e32555.*
Al-Obeidi, et al., "Design of a New Class of Superpotent Cyclic α-Melanotropins Based on Quenched Dynamic Simulations," Journal of American Chemical Society, 111: 3413-3416 (1989).
Bertolini, et al., "Brain effects of melanocortins," Pharmacological Research, 59: 13-47 (2009).
Branson, et al., "Binge Eating as a Major phenotype of Melanocortin 4 Receptor Gene Mutations," New England Journal of Medicine, 348: 1096-1103 (2003).
Brzoska, et al., "α-Melanocyte-Stimulating Hormone and Related Tripeptides: Biochemistry, Antiinflammatory and Protective Effects in Vitro and in Vivo, and Future Perspectives for the Treatment of Immune-Mediated Inflammatory Diseases," Endocrine Reviews, 295: 581-602 (2008).
Cai, et al., "Design of novel melanotropin agonists and antagonists with high potency and selectivity for human melanocortin receptors," Peptides, 26: 1481-1485 (2005).
Fehm, et al., "The Melanocortin Melanocyte-Stimulating Hormone/ Adrenocorticotropin4-10 Decreases Body Fat in Humans," The Journal of Clinical Endocrinology & Metabolism, 86: 1144-1148 (2001).
Franz, et al., "Evidence-Based Nutrition Priniciples and Recommendations for the Treatment and Prevention of Diabetes and Related Complications," Diabetes Care, 25(1): 148-198 (2002).
Garfield, et al., "Role of central melanocortin pathways in energy homeostasis," Trends in Endocrinology Metabolism, 20(5): 203-215 (2009).
Getting, et al., "Melanocortin peptide therapy for the treatment of arthritic pathologies," The Scientific World Journal, 9: 1394-1414 (2009).
Goodfellow, et al., "The Melanocortin System and its Role in Obesity and Cachexia," Current Topics in Medicinal Chemistry, 3: 855-883 (2003).
Ho, et al., "Functional Characterization of Mutations in Melanocortin-4 Receptor Associated with Human Obesity," The Journal of Biological Chemistry, 274(50): 35816-35822 (1999).
Huszar, et al., "Targeted Disruption of the Melanocortin-4 Receptor Results in Obesity in Mice," Cell, 88: 131-141 (1997).
Kask, et al., "Discovery of a Novel Superpotent and Selective Melanocortin-4 Receptor Antagonist (HS024): Evaluation in Vitro and in Vivo," Endocrinology, 139: 5006-5014 (1998).
Knowler, et al., "Reduction in the Incidence of the Type 2 Diabetes with Lifestyle Intervention or Metformin," The New England Journal of Medicine, 346(6):393-403 (2002).
Krude, et al., "Severe early-onset obesity, adrenal insufficiency and red hair pigmentation caused by POMC mutations in humans," Nature Genetics, 19: 155-157 (1998).
Maaser, et al., "Role of the Melanocortin System in Inflammation," Annals of the New York Academy of Science, 1072: 123-134 (2006).
Nijenhuis, et al., "Discovery and in vivo evaluation of anew melanocortin-4 receptor-selective peptides," Peptides, 24: 271-280 (2003).
Pierroz, et al., "Effects of Acute and Chronic Administration of the Melanocortin Agonists MTII in Mice with Diet-Induced Obesity," Diabetes, 51(5): 1337-1345 (2002).
Sawyer, et al., "[half-Cys$^4$, half-Cys$^{10}$]-α-Melanocyte-stimulating hormone: A cyclic α-melanotropin exhibiting superagonist biological activity," Proceedings of the National Academy of Science USA, 79: 1751-1755 (1982).
Schiöth, et al., "Selectivity of Cyclic [D-Nal$^7$and D-Phe$^7$] Substituted MSH Analogues for the Melanocortin Receptor Subtypes," Polypeptides, 18: 1009-1013 (1997).
Tuomilheto, et al., "Prevention of Type 2 Diabetes Mellitus by Changes in Lifestyle Among Subjects with Impaired Glucose Tolerance," The New England Journal of Medicine, 344(18): 1343-1350 (2001).
Vaisse, et al., "Melanocortin-4 receptor mutations are a frequent and heterogeneous cause of morbid obesity," Journal of Clinical Investigations, 106: 253-262 (2000).

(Continued)

*Primary Examiner* — Joanne Hama
*Assistant Examiner* — Ian Dang
(74) *Attorney, Agent, or Firm* — Kirk Baumeister

(57) ABSTRACT

The present invention relates to melanocortin receptor binding conjugates and methods of making and using the foregoing.

3 Claims, No Drawings

(56) References Cited

OTHER PUBLICATIONS

Wing, et al., "Long-term Effects of Modest Weight Loss in Type II Diabetic Patients," Archives of Internal Medicine, 147: 1749-1753 (1987).

Yaswen, et al., "Obesity in the mouse model of pro-opiomelanocortin deficiency responds to peripheral melanocortin," Nature Medicine, 5(9): 1066-1070 (1999).

Yeo, et al., "A frameshift mutation in MC4R associated with dominantly inherited human obesity," Nature Genetics, 20: 111-112 (1998).

PCT International Search Report dated Jun. 28, 2010.

Supplementary European Search Report sent Oct. 11, 2012.

Ruwe, et al., "Semi-rigid tripeptide agonists of melanocortin receptors," Bioorganic & Medicinal Chemistry Letters, 19: 5176-5181 (2009).

Todorovic, et al., "N-Terminal Fatty Acylated His-DPhe-Arg-Trp-$NH_2$ Tetrapeptides: Influence of Fatty Acid Chain Length on Potency and Selectivity at the Mouse Melanocortin Receptors and Human Melanocytes," Journal or Medicinal Chemistry, 48: 3328-3336 (2005).

\* cited by examiner

FUSION PROTEINS OF ALPHA-MSH DERIVATIVES AND FC

CROSS-REFERENCE TO RELATED APPLICATIONS

This application claims priority to U.S. Provisional Application Ser. Nos. 61/175,921, filed 6 May 2009 and 61/176,294, filed 7 May 2009. The entire contents of each of the aforementioned provisional applications is incorporated herein by reference in their entireties.

FIELD OF THE INVENTION

The present invention relates to melanocortin receptor binding conjugates and methods of making and using the foregoing.

BACKGROUND OF THE INVENTION

Obesity is a chronic disease manifested by an excess of fat mass in proportion to body size. Today, every third American is considered overweight (Body Mass Index (BMI)>25 kg/m$^2$). Obesity predisposes to Type 2 Diabetes, congestive heart failure, osteoarthritis, sleep apnea, Metabolic Syndrome, atherogenic dyslipidemia, elevated blood pressure and insulin resistance. Even a modest decrease in body weight (5-10% of initial body weight) may significantly lower the risk factors for developing obesity-associated diseases (Wing et al., Arch. Intern. Med. 147:1749-53 (1987); Tuomilehto et al., New Engl. J. Med. 344:1343-50 (2001); Knowler et al., New Engl. J. Med. 346:393-403 (2002); Franz et al., Diabetes Care 25:148-98 (2002)). Additionally, treatment of obesity may be important from a mental health perspective due to the social stigma often attached to obese individuals in some cultures.

The melanocortin system plays a major role in the regulation of energy balance and food intake (Garfield et al., Trends Endocrinol Metab. 20:203-15 (2009)). In humans and rodents, loss of function mutations in the different components of the melanocortin system are closely correlated with obesity and related conditions. In mice, mutations within the melanocortin receptor 4 (MC4R), melanocortin receptor 3 (MC3R) or pro-opiomelanocortin (POMC) produce obesity, insulin resistance and hyperphagia (Goodfellow and Saunders, Curr. Topics Med. Chem. 3:855-83 (2003); Huszar et al., Cell 88:131-41 (1997); Yaswen et al., Nat. Med. 5:1066-70 (1999)). In man, mutations within POMC or MC4R lead to the development of obesity associated with increased food intake (Krude et al., Nat. Genet. 19:155-7 (1998); Yeo et al., Nature Genetics 20:111-2 (1998); Branson et al., New Engl. J. Med. 348:1096-103 (2003); Vaisse et al., J. Clin. Invest. 106:253-62 (2000); Ho and MacKenzie, J. Biol. Chem. 275:35816-22 (1999)). Pharmacological stimulation of MC4R leads to decreased food intake, increased energy expenditure and weight loss in rodents (Pierroz et al., Diabetes 51:1337-45 (2002)). In man, the intranasal administration of MC4R agonist alpha-MSH results in decreased body weight due to the decreased fat mass (Fehm et al., J. Clin. Endo. Metabol. 86:1144-48 (2001)). The wild type alpha-MSH is of limited use as a pharmaceutical due to its extremely short serum half-life. Alpha-MSH analogs have been described (Cai et al., Peptides 26:1481-5, (2005); Al-Obeidi t al., J. Am. Chem. Soc. 111:3413-3416 (1989); Kask et al., Endocrinology 139:5006-5014 (1998); Nijenhuis et al., Peptides 24:271-80, (2003); Schoth et al., Peptides 18:1009-13 (1997), Pat. Appl. No. WO06/073772; U.S. Pat. No. 6,716,810).

Alpha-MSH has potent anti-inflammatory effects mediated by centrally expressed melanocortin receptors. At the molecular level, alpha-MSH beneficially modulates various pathways implicated in regulation of inflammation and protection, such as NF-kB activation, production of proinflammatory cytokines and mediators, IL-10 synthesis, T cell and inflammatory cell proliferation and activity, inflammatory cell migration, expression of antioxidative enzymes, and apoptosis. The antiinflammatory effects of alpha-MSH have been validated in several inflammatory animal models ((for review see Brzoska et al., Endocr Rev. 29:581-602 (2008); Getting et al., Scientific World Journal. 9:1394-414 (2009), Maaser et al., Ann N Y Acad. Sci. 1072:123-34 (2006)).

In recent years, the pro-opiomelanocortin (POMC)-derived peptides (melanocortins, e.g. alpha-MSH, beta-MSH and gamma-MSH, and adrenocorticotrophic hormone (ACTH)) having in common the tetrapeptide sequence His-Phe-Arg-Trp have been implicated in a plethora of diseases such as sexual impotence, frigidity, anorexia, cachexia, haemorrhagic shock, myocardial infarction, ischemia, neuropathic pain, rheumathoid arthritis, inflammatory bowel disease, nerve injury and neuropathies, by acting via different melanocortin receptors (for review Bertolini et al., Pharmacol Res. 59:13-47 (2009); Brzoska et al., Endocrine Rev. 29:581-602 (2008)).

Thus, a need exists to develop additional melanocortin receptor binding conjugates to treat obesity and other melanocortin system-mediated conditions.

SUMMARY OF THE INVENTION

One aspect of the invention is an alpha-MSH derivative-Fc conjugate, wherein the conjugate has a structure shown in formula I:

$$B\text{-}(L)n\text{-}(X)m\text{-}(D)p\text{-CH2-CH3}, \qquad (I),$$

wherein B is an alpha-MSH derivative;
L is a linker;
X is any naturally occurring amino acid.
D is at least a portion of an immunoglobulin hinge region;
CH2 is at least a portion of an immunoglobulin CH2 constant domain;
CH3 is at least a portion of an immunoglobulin CH3 constant domain;
n is 0 or 1;
m is from 0 to 20; and
p is 0 or 1.

Another aspect of the invention is a pharmaceutical composition comprising the alpha-MSH derivative-Fc of claim 1 in combination with a pharmaceutically acceptable carrier.

Another aspect of the invention is a method of modulating a biological activity of a melanocortin receptor, comprising contacting the pharmaceutical composition of claim 1 with the melanocortin receptor.

Another aspect of the invention is a method of modulating the melanocortin receptor-mediated condition, comprising administering the pharmaceutical composition of the invention to a patient in need thereof.

DETAILED DESCRIPTION OF THE INVENTION

All publications, including but not limited to patents and patent applications, cited in this specification are herein incorporated by reference as though fully set forth.

The term "alpha-MSH derivative" as used herein refers to a fragment, homolog, or analog of the "wild type alpha-MSH", and has at least one non-naturally occurring amino acid incorporated into the derivative. An alpha-MSH fragment is a peptide obtained after truncation of one or more amino acids from the N-terminus and/or C-terminus of the wild type alpha-MSH or an analog thereof. An alpha-MSH homolog is a peptide in which one or more amino acids have been added to the N-terminus and/or C-terminus of the wild type alpha-MSH, or fragments or analogs thereof. An alpha-MSH analog is a peptide in which one or more amino acids of the wild type alpha-MSH or fragment have been modified and/or substituted. An alpha-MSH derivative has sufficient homology to the wild type alpha-MSH as long as the analog at least partially retains the biological activity of the wild-type alpha-MSH. The alpha-MSH derivative may be a cyclic peptide, or have chemical modification of at least one amino acid side group, α-carbon atom, terminal amino group, or terminal carboxylic acid group. The "wild type alpha-MSH" is a 13 amino acid peptide processed from the precursor pro-opiomelanocortin (POMC), and binds with high affinity to the MC4R, and at lower affinity to the MC3R and MC5R. The "wild type alpha-MSH" has an amino acid sequence shown in SEQ ID NO: 1. Alpha-MSH derivatives can retain substantially the same, or a subset, of the biological activities of the wild type alpha-MSH.

"Melanocortin receptor" as used herein refers to the family of human melanocortin receptors comprising of melancortin 1 receptor (MC1R) (SEQ ID NO: 5), melanocortin 2 receptor (MC2R) (SEQ ID NO: 9), melanocortin 3 receptor (MC3R) (SEQ ID NO: 6), melanocortin 4 receptor (MC4R) (SEQ ID NO: 7), and melanocortin 5 receptor (MC5R) (SEQ ID NO: 8).

The terms "peptide" and "protein" are used interchangeably to refer to two or more amino acid residues linked together by amide bonds. The term is meant to include proteins, polypeptides, and peptides of any size, structure, or function. Typically, a peptide will be at least six amino acids long and a protein will be at least 50 amino acids long.

The term "conjugate" as used herein refers to the molecule formed as a result of covalent attachment of an alpha-MSH derivative to a Fc portion of an antibody. The alpha-MSH derivative can be coupled from the N-terminus or the C-terminus of the derivative to the C-terminus or N-terminus of the Fc portion, respectively, or from an internal amino acid. An optional linker may be inserted between the alpha-MSH derivative and the Fc portion. Exemplary covalent attachment of the alpha-MSH and the Fc can be done by a hydrazone or semicarbazone linkage.

The terms "Fc" or "Fc portion" as used herein refers to one of the well characterized fragments produced by digestion of an antibody with various peptidases, for example pepsin, and can include an antibody hinge region, and includes at least a portion of a hinge region, CH2, and CH3 domains.

The term "linker" (L) as used herein refers to an atom or a collection of atoms used to link alpha-MSH derivative and the Fc for example by one or more covalent bonds.

"Non-naturally occurring" or "unnatural" amino acid are used interchangeably and refer to amino acids not present in proteins isolated from nature. Exemplary non-naturally occurring amino acids are shown in Table 1, and also include D-amino acids, 3-amino acids, pseudo-glutamate, γ-aminobutyrate, homocysteine, N-substituted amino acids (Simon et al., Proc. Natl. Acad. Sci. U.S.A. 89:9367-71 (1992); WO91/19735, U.S. Pat. No. 5,646,285), α-aminomethyl-eneoxy acetic acids (an amino acid-Gly dipeptide isostere), and α-aminooxy acids and other amino acid derivatives having non-genetically non-encoded side chain function groups.

The term "ethylene glycol unit" as used herein refers to linear oligomers composed of repeating ethyleneoxy units. The termini of the ethyleneoxy units can be functionalized by the addition of amino and carboxylic acid groups and derivatives thereof. An exemplary amino group is a hydrazine.

"Increase in serum half-life" or "increased $t_{1/2}$" as used herein refers to the positive change in circulating half-life of a modified biologically active molecule relative to its non-modified form. Serum half-life of proteins can be determined in humans or in animal models, such as *Macaca fascicularis* or *Papio cynocephalus* (cynomolgus monkey). An exemplary increase in serum half-life is about two-fold, but a smaller increase may be useful.

The present invention relates to alpha-MSH derivative-Fc conjugates that incorporate non-naturally occurring amino acids or additional organic moieties in the alpha-MSH derivative, that can result in improved properties in the alpha-MSH derivative-Fc conjugates.

TABLE 1

| Non-natural amino acid | Symbol |
| --- | --- |
| 2-Aminoadipic acid | Aad |
| beta-Alanine, beta-Aminopropionic acid | bAla |
| 2-Aminobutyric acid | Abu |
| 4-Aminobutyric acid, piperidinic acid | 4Abu |
| 6-Aminocaproic acid | Acp |
| 2-Aminoheptanoic acid | Ahe |
| 2-Aminoisobutyric acid | Aib |
| 2-Aminopimelic acid | Apm |
| 2,4-Diaminobutyric acid | Dbu |
| Desmosine | Des |
| 2,2'-Diaminopimelic acid | Dpm |
| 2,3-Diaminopropionic acid | Dpr |
| N-Ethylglycine | EtGly |
| N-Ethylasparagine | EtAsn |
| Hydroxylysine | Hyl |
| allo-Hydroxylysine | AHyl |
| 3-Hydroxyproline | 3Hyp |
| 4-Hydroxyproline | 4Hyp |
| Isodesmosine | Ide |
| allo-Isoleucine | AIle |
| N-Methylglycine, sarcosine | MeGly |
| N-Methylisoleucine | MeIle |
| 6-N-Methyllysine | MeLys |
| N-Methylvaline | MeVal |
| Norvaline | Nva |
| Norleucine | Nle |
| Ornithine | Orn |

One embodiment of the invention is an alpha-MSH-Fc conjugate, wherein the conjugate has a structure shown in formula I:

$$B\text{-}(L)n\text{-}(X)m\text{-}(D)p\text{-}CH2\text{-}CH3, \quad (I),$$

wherein B is an alpha-MSH,

L is a linker,

X is a naturally occurring amino acid,

D is at least a portion of an immunoglobulin hinge region,

CH2 is at least a portion of an immunoglobulin CH2 constant domain,

CH3 is at least a portion of an immunoglobulin CH3 constant domain, n is 0 or 1;

m is from 0 to 20; and p is 0 or 1.

In other embodiments of the invention, the alpha-MSH derivative has a structure shown in Formula II (SEQ ID NO: 10):

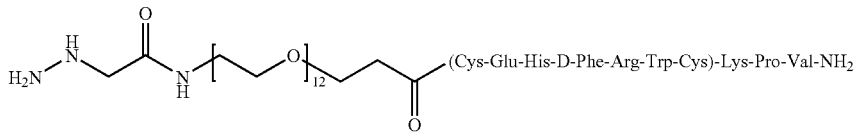

II

In other embodiments of the invention, the alpha-MSH derivative has a structure shown in Formula III (SEQ ID NO: 11):

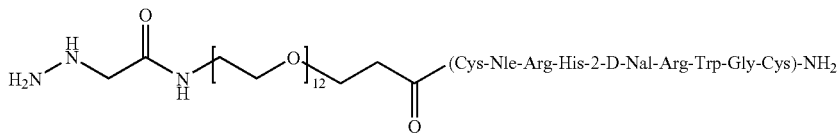

III

In other embodiments of the invention, the alpha-MSH derivative has a structure shown in Formula IV (SEQ ID NO: 12):

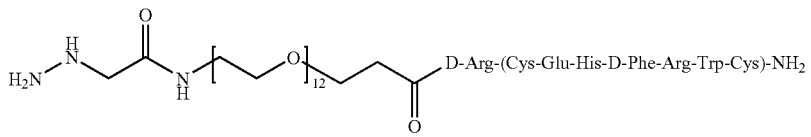

IV

In other embodiments of the invention, the alpha-MSH derivative has a structure shown in Formula V (SEQ ID NO: 13):

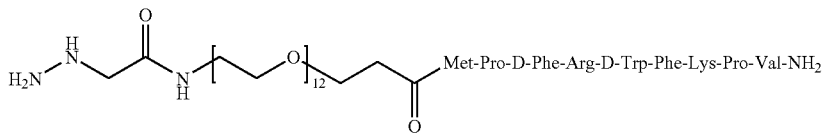

V

In other embodiments of the invention, the alpha-MSH derivative has a structure shown in Formula VI (SEQ ID NO: 14):

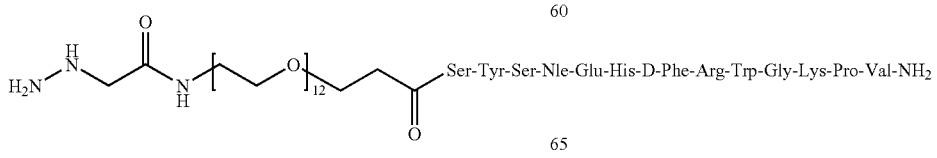

VI

In other embodiments of the invention, the alpha-MSH derivative has a structure shown in Formula VII (SEQ ID NO: 15):

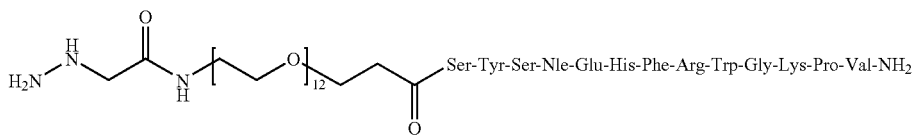

VII

In other embodiments of the invention, the alpha-MSH derivative has a structure shown in Formula VIII (SEQ ID NO: 16):

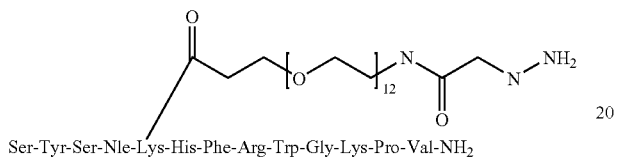

VIII

Ser-Tyr-Ser-Nle-Lys-His-Phe-Arg-Trp-Gly-Lys-Pro-Val-NH₂

In other embodiments of the invention, the alpha-MSH derivative has a structure shown in Formula IX (SEQ ID NO: 17):

IX

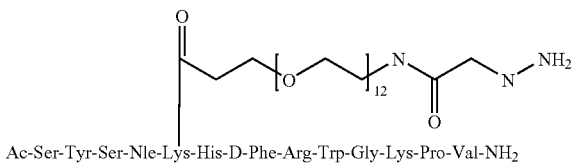

Ac-Ser-Tyr-Ser-Nle-Lys-His-Phe-Arg-Trp-Gly-Lys-Pro-Val-NH₂

In other embodiments of the invention, the alpha-MSH derivative has a structure shown in Formula X (SEQ ID NO: 18):

X

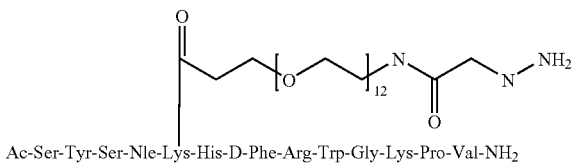

Ac-Ser-Tyr-Ser-Nle-Lys-His-D-Phe-Arg-Trp-Gly-Lys-Pro-Val-NH₂

In other embodiments of the invention, the alpha-MSH derivative has a structure shown in Formula XI (SEQ ID NO: 19):

XI

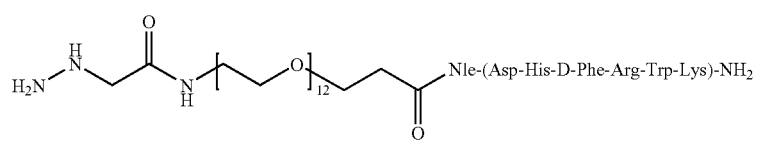

In other embodiments of the invention, the alpha-MSH derivative has a structure shown in Formula XII (SEQ ID NO: 20):

XII

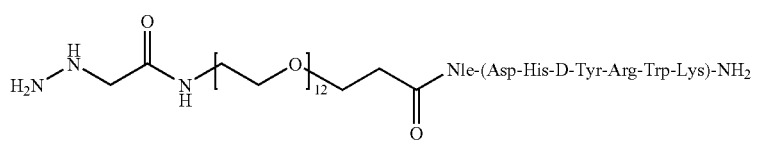

In other embodiments of the invention, the alpha-MSH derivative has a structure shown in Formula XIII (SEQ ID NO: 21):

XIII

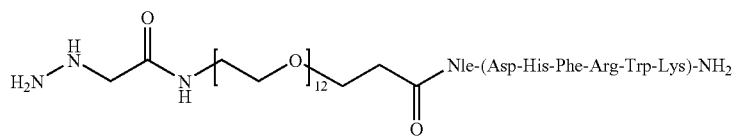

Nle-(Asp-His-Phe-Arg-Trp-Lys)-NH$_2$

In other embodiments of the invention, the alpha-MSH derivative has a structure shown in Formula XIV (SEQ ID NO: 22):

XIV

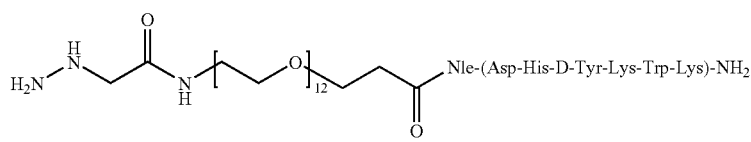

Nle-(Asp-His-D-Tyr-Lys-Trp-Lys)-NH$_2$

In other embodiments of the invention, the alpha-MSH derivative has a structure shown in Formula XV (SEQ ID NO: 23):

XV

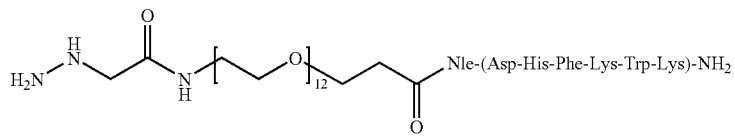

Nle-(Asp-His-Phe-Lys-Trp-Lys)-NH$_2$

The alpha-MSH derivative can be produced by for example chemical synthesis or recombinant expression or a combination thereof, using well known methods. For solid phase peptide synthesis, t-Boc (tert-Butyloxy carbonyl) and Fmoc (Fluorenyl-methoxy-carbonyl) chemistry, referring to the N-terminal protecting groups, on polyamide or polystyrene resin can be used (Merrifield, Ann N Y Acad. Sci. 104:161-71 (1963)).

For recombinant production, non-naturally occurring amino acid residues can be introduced using for example codon suppression to introduce an aldehyde or ketone functional group in any suitable position within alpha-MSH derivative or by expressing the alpha-MSH derivative in the Pseudomonas host cells (Pat. Appl. No. WO06/132969). Exemplary non-naturally occurring amino acids are discussed above.

Amino acids in a polypeptide that are essential for function can be identified by well known methods, for example generating variants using chemical synthesis or using site-directed mutagenesis, and testing the variants for desired biological activity, such as the ability to induce signaling downstream through a cognate receptor.

The alpha-MSH derivative can further be modified by covalent attachment of at least one organic moiety to, for example, improve pharmacokinetic properties of the molecule. The organic moiety can be, for example, fatty acid, fatty acid ester, polyalkane glycol including polyethylene glycol (PEG), carbohydrate polymer, amino acid polymer or polyvinyl pyrolidone. The fatty acid and the fatty acid ester can comprise from about 8-40 carbon atoms. Exemplary fatty acids are laurate, myristate, stearate, arachidate, behenate, n-triacontanoate, n-tetracontanoate, oleate, arachidonate, octanedioic acid, tetradecanedioic acid, octadecanedioic acid, and docosanedioic acid. The polyalkane glycol can have a molecular weight of about 800 to about 120,000 Daltons. The polyethyleneglygol (PEG) can have a molecular weight of between about 100-5000 kD, or between about 100-500 kD. The PEG, fatty acids and their esters can be derivatized with terminal amino, hydroxyl, mercapto, and/or carboxy groups. The organic moiety can be coupled to the alpha-MSH derivative using well know methods (Hermanson, Bioconjugate Techniques, Academic Press: San Diego, Calif. (1996); Kolb, Finn and Sharpless, "Click Chemistry: Diverse Chemical Function from a Few Good Reactions". Angewandte Chemie International Edition 40:2004-21 (2001); Evans, Australian J. Chem. 60:384-95 (2007)). Exemplary methods for selective attachment of PEG have been described (Pat. Appl. No. WO99/45026, Pat. Appl. No. WO 99/03887, U.S. Pat. No. 5,206,344 and U.S. Pat. No. 5,766,897).

The Fc portion of the alpha-MSH derivative-Fc conjugates of the present invention can be derived from an intact naturally occurring isolated antibody after for example papain cleavage, or can be synthesized de novo recombinantly or chemically using standard methods. The sequences of human and animal immunoglobulins can be found at the ImMunoGeneTics database (http://www imgt org) or at Kabat, et al. Sequences of Proteins of Immunological Interest, U.S. Dept. Health (1983). Sequences derived from human germline information as well as known and useful therapeutic human antibody sequences and variations thereof have been summarized in Pat. Appl. No. WO05/005604. The Fc portion may be derived from any immunoglobulin class, e.g. IgA$_1$, IgA$_2$, IgD, IgE, IgG$_1$, IgG2$_1$, IgG3$_1$, IgG2$_4$, and IgM heavy chains. Exemplary Fc portions have amino acid sequences shown in SEQ ID NOs: 2-3. The Fc portion may be produced in a glycosylated or non-glycosylated form by expressing the Fc in mammalian or prokaryotic cells, respectively. The glycosylated antibodies are more resistant to papain digestion than the deglycosylated or aglycosylated or non-glycosylated antibodies, thus the deglycosylation step should be performed following papain digestion when producing Fc portions from naturally occurring isolated antibodies.

The Fc domain mediates antibody effector functions such as complement binding and antibody-dependent cell cytoxicity (ADCC). Certain natural and synthetic variants of the Fc-region polypeptides sequences with altered effector functions include mutant polypeptides as described in, for example, U.S. Pat. No. 5,624,821, U.S. Pat. No. 6,528,624, U.S. Pat. No. 7,122,637, U.S. Pat. No. 7,183,387. Antibody effector functions can also be dependent on the presence of the glycans attached to the Fc in the CH2 domain (Jefferis & Lund, Immunol. Letters. 82:57-65, (2002)). The non-glycosylated Fc domains incapable of inducing effector functions can be generated by expressing the Fc domains recombinantly in bacterial host cell, or the glycans can be removed enzymatically using glycosidases.

The alpha-MSH derivative may be conjugated to at least one Fc portion in an immunoglobulin, optionally via the linker. Non-identical alpha-MSH derivatives can be conjugated to the Fc portion when more than one alpha-MSH derivative is conjugated. Conjugation can be done from any residue on the alpha-MSH derivative so long as the final alpha-MSH derivative-Fc conjugate displays the desired biological activity. Biological activity may be measured by in vitro assays, for example binding activity, by in vivo activity such as in animal models of disease, or by the response of a subject following administration of the conjugate. Exemplary biological activity measures increase in intracellular cAMP upon MC4R stimulation as described in the Examples.

The conjugation of the alpha-MSH derivative to the Fc portion can be done for example by reductive alkylation between a nucleophilic group that has been introduced into the alpha-MSH derivative and a reactive carbonyl in the Fc. Exemplary nucleophilic groups are a primary amine, hydrazine, acyl hydrazide, carbazide, semicarbazide or thiocarbazide groups. Exemplary carbonyl groups are an aldehyde or ketone groups. The nucleophilic group can be attached to the N-terminus of the derivative, the C-terminus of the derivative or any side chain containing an amino, hydroxyl, thiol, carboxylic acid or carboxamide functionality, to a similar group on a non-natural amino acid, or to an organic moiety attached to the alpha-MSH derivative. The activation of the alpha-MSH derivative for conjugation to the Fc-domain can be done during the solid phase synthesis using tri-Boc-hydrazinoacetic acid at the final residue prior to cleavage from the resin to give the hydrazine derivatized alpha-MSH derivative.

The N-terminal residue of the Fc portion is prepared for conjugation by creating a reactive (electrophilic) carbonyl from for example aldehydes or ketones. Fc portions containing an N-terminal threonine (Thr) or serine (Ser), e.g. a reactive carbonyl, can be oxidized with periodic acid to give N-terminal glycoxylic acid derivatives (Geoghegan and Stroh, Bioconjugate Chem. 3:138-46 (1992); U.S. Pat. No. 5,362,852; Garnter et al., Bioconjugate Chem. 7:38-44, (1996); Pat. Appl. No. WO98/05363; U.S. Pat. Appl. No. US09/0181037). The Fc portion may naturally have a serine or threonine or may be engineered or chemically altered to display a serine or threonine at the N-terminus by well known methods, for example by synthesis of glyoxylyl peptides using an Fmoc-protected α,α'-diaminoacetic acid derivative ((Fmoc-NH)$_2$CHCO$_2$H) (Far and Melnyk, J. Peptide Sci. 11:424-30, 2005). Alternatively, the N-terminal Ser or Thr residue can be generated in proteins by utilizing reverse proteolysis using trypsin or carboxypeptidase Y (Rose et al., Biochem J. 211:671-6 (1983)), or the glyoxyl transamination reaction can be used to generate an aldehyde ((Dixon and Fields, Methods Enzymol. 25:409-19 (1979), U.S. Pat. No. 6,077,393).

If the Fc contains N- or O-linked glycosyl groups, the carbohydrate is susceptible to oxidation by oxidizing agents used to affect the formation of the N-terminal glyoxal group, producing additional reactive carbonyl species. Carbohydrates can be removed prior to chemical linking using PNGase followed by purification by hydrophobic interaction HPLC.

The stochiometry of incorporation can be controlled by adjusting the stochiometry of the reaction or by incorporating and controlling suitable steric interactions.

An exemplary alpha-MSH derivative-Fc conjugate is formed by oxidizing the N-terminal Thr of IgG$_1$ Fc to form glyoxylate, conjugating the oxidized Fc with the alpha-MSH derivative of Formula IX via a hydrazine bond in the attached organic moiety (PEG), followed by NaBH$_3$CN reduction to stabilize the conjugate.

The alpha-MSH derivative may be conjugated to the Fc via a linker. Exemplary linkers include alkyl linkers such as —NH—(CH$_2$)$_s$—C(O)—, wherein s=2-20. The alkyl linkers may further be substituted by any non-sterically hindering group such as lower alkyl (e.g., C$_1$-C$_6$) lower acyl, halogen (e.g., Cl, Br), CN, NH$_2$, or phenyl. Exemplary polymer linkers are polyethylene glycol (PEG), polyvinyl pyrrolidone, polyvinyl alcohol, polyamino acids, divinylether maleic anhydride, N-(2-Hydroxypropyl)-methacrylamide, dextran, dextran derivatives including dextran sulfate, polypropylene glycol, polyoxyethylated polyol, heparin, heparin fragments, polysaccharides, cellulose and cellulose derivatives, including methylcellulose and carboxymethyl cellulose, starch and starch derivatives, polyalkylene glycol and derivatives thereof, copolymers of polyalkylene glycols and derivatives thereof, polyvinyl ethyl ethers, and α,β-Poly[(2-hydroxyethyl)-DL-aspartamide, and the like, or mixtures thereof. The polyethyleneglycol (PEG) linker can have the same properties as described above for the PEG modification of the alpha-MSH.

The linker may include polymer chains or units that are biostable or biodegradable. For example, polymers with repeat linkages may have varying degrees of stability under physiological conditions depending on bond lability. Polymers with such bonds can be categorized by their relative rates of hydrolysis under physiological conditions based on known hydrolysis rates of low molecular weight analogs, e.g., from less stable to more stable polycarbonates (—O—C(O)—O—)>polyesters (—C(O)—O—)>polyurethanes (—NH—C(O)—O—)>polyorthoesters (—O—C((OR)(R'))—O—)>polyamides (—C(O)—NH—). Similarly, the linkage systems attaching a water-soluble polymer to a target molecule may be biostable or biodegradable, for example, from less stable to more stable carbonate (—O—C(O)—O—)>ester (—C(O)—O—)>urethane (—NH—C(O)—O—)>orthoester (—O—C((OR)(R'))—O—)>amide (—C(O)—NH—).

The linker can be added to the alpha-MSH derivative during solid phase synthesis, by coupling the linker having protected bi-functional groups for example to the deprotected N-terminal amino group or any other amino acid having side chain amino group (for example, lysine, diamino butyric acid, and 4-amino phenylalanine) of the alpha-MSH derivative. The linker can be conjugated at the C-terminus of the alpha-MSH derivative by direct coupling of the linker to the resin, followed by assembly of the peptide and cleavage of the alpha-MSH derivative-linker from the resin by hydrazine or a hydrazine derivative. The peptide may also be prepared on a resin such as the Universal PEG NovaTag resin (Novabiochem). The methods of coupling are well known.

The alpha-MSH derivative-Fc conjugate may include one or more naturally occurring amino acids (X) between the linker (L) and the hinge (D), as shown in Formula I. The amino acids between the linker and the hinge are typically derived from a variable region of an antibody, and are inserted to increase the distance between the alpha-MSH derivative and the Fc, thereby facilitating proper conformational structure and activity of the alpha-MSH derivatives. Exemplary naturally occurring amino acids in the alpha-MSH derivative-Fc conjugate can be a peptide having a sequence GTLVTVSS (SEQ ID NO: 4). The sequence may be derivatized to allow covalent bond formation with the linker.

Methods of Treatment

The alpha-MSH derivative-Fc conjugates of the present invention can be used to treat a wide variety of diseases and conditions. While not wishing to be bound by any particular theory, the alpha-MSH-Fc conjugates of the invention may stimulate the melanocortin system by agonizing the MC3R and/or the MC4R. The methods of the invention may be used to treat a subject belonging to any classification. Examples of such subjects include mammals such as humans, rodents, dogs, cats and farm animals. For example, the alpha-MSH-Fc conjugates of the invention are useful in agonizing melanocortin receptors, in the treatment of obesity, type II diabetes, and metabolic syndrome, and are also useful in the preparation of a medicament for such treatment wherein the medicament is prepared for administration in dosages defined herein.

Disease and conditions that may be treated by administration of the alpha-MSH derivative-Fc conjugates of the present invention include type I diabetes, type II diabetes, stroke (Pat. Appl. No. WO00/16797), myocardial infarction (Pat. Appl. No. WO98/08531), obesity (Pat. Appl. No. WO98/19698), catabolic changes after surgery (U.S. Pat. No. 6,006,753), functional dyspepsia and irritable bowel syndrome (Pat. Appl. No. WO99/64060). Subjects with impaired glucose tolerance, impaired fasting glucose, overweight subjects with body weight index (BMI) over 25, subjects with a partial pancreatectomy or gestational diabetes, and subjects who have had acute or chronic pancreatitis may be treated with alpha-MSH derivative-Fc conjugates of the present invention. Also included are subjects requiring prophylactic treatment with an MSH compound, for example, subjects at risk for developing non-insulin dependent diabetes (Pat. Appl. No. WO00/07617).

Specific biological effects can be elicited by treatment with an alpha-MSH derivative of limited function. Treatment of a subject with an alpha-MSH derivative having a subset of the biological activities of the wild type alpha-MSH can have fewer side effects in a subject relative to treatment with the naturally occurring form of the protein.

Administration/Pharmaceutical Compositions

The "therapeutically effective amount" of the alpha-MSH derivative-Fc conjugate in the treatment or prevention of conditions where modulation of the melanocortin system is desirable can be determined by standard research techniques. For example, the dosage of the agent that will be effective in the treatment or prevention of obesity, diabetes or insulin resistance can be determined by administering the agent to relevant animal models.

In addition, in vitro assays can optionally be employed to help identify optimal dosage ranges. Selection of a particular effective dose can be determined (for example, via clinical trials) by those skilled in the art based upon the consideration of several factors. Such factors include the disease to be treated or prevented, the symptoms involved, the patient's body mass, the patient's fasting glucose and insulin and other factors known by the skilled artisan. The precise dose to be employed in the formulation will also depend on the route of administration, and the severity of disease, and should be decided according to the judgment of the practitioner and each patient's circumstances. Effective doses can be extrapolated from dose-response curves derived from in vitro or animal model test systems.

In the methods of the invention, the alpha-MSH-Fc conjugates may be administered singly or in combination with at least one other molecule. Such additional molecules may be other melanocortin receptor agonists or molecules with a therapeutic benefit not mediated by melanocortin receptor signaling. Small molecules that reduce body weight or improve insulin resistance are examples of such additional molecules.

The mode of administration for therapeutic use of the alpha-MSH derivative-Fc conjugates of the invention may be any suitable route that delivers the alpha-MSH derivative-Fc conjugates to the host. Pharmaceutical compositions of the alpha-MSH derivative-Fc conjugates can be administrated using for example oral, rectal, nasal, lower respiratory, intramuscular, intravenous or subcutaneous routes.

The alpha-MSH derivative-Fc conjugates of the invention may be prepared as pharmaceutical compositions containing an effective amount of the alpha-MSH derivative-Fc conjugate as an active ingredient in a pharmaceutically acceptable carrier. The term "carrier" refers to a diluent, adjuvant, excipient, or vehicle with which the active compound is administered. Such pharmaceutical vehicles can be liquids, such as water and oils, including those of petroleum, animal, vegetable or synthetic origin, such as peanut oil, soybean oil, mineral oil, sesame oil and the like. For example, 0.4% saline and 0.3% glycine can be used. These solutions are sterile and generally free of particulate matter. They may be sterilized by conventional, well-known sterilization techniques (e.g., filtration). The compositions may contain pharmaceutically acceptable auxiliary substances as required to approximate physiological conditions such as pH adjusting and buffering agents, stabilizing, thickening, lubricating and coloring agents, etc. The concentration of the alpha-MSH derivative-Fc conjugates of the invention in such pharmaceutical formulation can vary widely, i.e., from less than about 0.5%, usually at or at least about 1% to as much as 15 or 20% by weight and will be selected primarily based on required dose, fluid volumes, viscosities, etc., according to the particular mode of administration selected.

Thus, a pharmaceutical composition of the invention for intramuscular injection could be prepared to contain 1 ml sterile buffered water, and between about 1 ng to about 100 mg, e.g. about 50 ng to about 30 mg or more preferably, about 5 mg to about 25 mg, of the alpha-MSH derivative-Fc conjugate of the invention. Similarly, a pharmaceutical composition of the invention for intravenous infusion could be made up to contain about 250 ml of sterile Ringer's solution, and about 1 mg to about 30 mg and preferably 5 mg to about 25 mg of the alpha-MSH derivative-Fc of the invention. Actual methods for preparing parenterally administrable compositions are well known and are described in more detail in, for example, "Remington's Pharmaceutical Science", 15th ed., Mack Publishing Company, Easton, Pa.

The alpha-MSH derivative-Fc conjugates of the invention can be lyophilized for storage and reconstituted in a suitable carrier prior to use. This technique has been shown to be effective with other protein preparations and art-known lyophilization and reconstitution techniques can be employed.

While having described the invention in general terms, the embodiments of the invention will be further disclosed in the following examples.

Example I

Synthesis of Alpha-MSH Derivatives

The peptides were prepared on an ABI 433A Peptide Synthesizer using SynthAssist 2.0 Version for Fmoc/HBTU chemistry by the Fastmoc 0.1 mM Monitoring Previous Peak software.

Peptides of Formulae II-IV.

NovaSyn TGR Novabiochem amide resin (0.1 mmol) was used in the synthesis. The final two amino acids derivatives in the synthesis were tri-BOC-hydrazinoacetic acid and O—(N-Fmoc-2-aminoethyl)-O'-(2-carboxyethyl)-undecaethyleneglycol.

After synthesis, the resin was washed 3×2 min with N-methylpyrrolidone, 1×2 min with methylene chloride/N-methylpyrrolidone, 3×2 min with methylene chloride, 3×2 min with methanol, 1×2 min with ethyl ether and dried under reduced pressure for two hours.

The peptides were cleaved from the resin by stirring in a scintillation vial using 20 mL of a cleavage mixture of trifluoroacetic acid (30 mL), phenol (2.25 g), dithiothrietol (1.5 g), thioanisole (1.5 mL), triisopropylsilane (1.5 mL), and water (1.5 mL) for four hours at ambient temperature. The resin was removed by filtration and the peptide was precipitated by the addition of precooled ethyl ether (600 mL). The resulting solid was isolated by filtration and washed with ethyl ether and dried under reduced pressure. For synthesis of some peptides, 15 ml of cleavage mixture was used and the peptides precipitated with 400 mL precooled ethyl ether.

Peptide Cyclization

The crude material from the cleavage was dissolved in 50 ml of water with a trace of acetic acid. 600 ml of water was adjusted to pH 8.0 with 1 M $NH_4OH$. A solution of 0.01M $K_3Fe(CN)_6$ was prepared in water. Over the course of 4 hours, aliquots of the peptide were added to the water and the pH adjusted to 8.0 with 1 M $NH_4OH$. Aliquots of the ferricyanide solution were added to maintain a light yellow color. After the addition, the solution was stirred for an additional hour. To the solution was added 50 ml of BioRad AG-4-X3, 100-200 mesh, free base form. The solution was stirred for 1 hour and the resin removed by filtration. The filtrate was lyophilized to give the crude cyclic peptide.

The crude peptide was purified on two Vydac C-18 columns (10 mm, 2.5×25 cm), using a gradient of 0-100%, 10-90% or 10-80%, depending on a peptide (Buffer A=0.1% trifluoroacetic acid in water, Buffer B=0.1% trifluoroacetic acid in 80% acetonitrile/20% water (GAH) in water) over 60 min at a flow rate of 6 mL/min. Fractions were collected, analyzed by HPLC and the pure fractions pooled and lyophilized.

Peptides of Formulae V-VII.

Synthesis and purification was done as describe for Formulae II-IV peptides, except that the cyclization step was omitted.

Peptides of Formulae VIII and IX.

0.25 mmol NovaSyn TGR Novabiochem amide resin was used in the synthesis. For $Lys^5$, DDE-Lys(FMOC) was used. After the coupling of DDE-Lys(FMOC), tri-BOC-hydrazinoacetic acid and O—(N-Fmoc-2-aminoethyl)-O'-(2-carboxyethyl)-undecaethyleneglycol were added. The DDE group was removed by treating the resin in a manual shaker 4×2 minutes with a solution of 2% anhydrous hydrazine in DMF. The resin was returned to the synthesizer and the final four amino acids were coupled and the N-terminal FMOC group removed.

The peptides were cleaved from the resin by stirring in a scintillation vial using 15 ml of a mixture of 20 ml of trifluoroacetic acid, 3 g of phenol, 6 ml of ethanedithiol, 1 ml of thioanisole and 1 ml of water for 4 hr at ambient temperature. The resin was removed by filtration and the peptide was precipitated by the addition of precooled ethyl ether (200 mL), and the peptides were purified as described above.

Peptide of Formula X. 0.50 g of 0.20 meq/g NovaSyn TGR Novabiochem amide resin was used. The protecting groups used were N-terminal FMOC, His(Trt), Arg(Pmc), Ser(t-Bu), Lys(BOC) and Lys(DDE). Deprotection was with 5% DBU in piperidine, diluted according to the FastMoc program. The residues were coupled to give Ser(O-t-Bu)-Tyr(BOC)-Ser(O-t-Bu)-Nle-Lys(DDE)-His(Trt)-Phe-Arg(Pmc)-Trp(BOC)-Gly-Lys(BOC)-Pro-Val-Resin. The resin was acetylated manually by treatment for 10 minutes with a solution of 1 ml acetic anhydride, 9 ml DMF and 0.1 ml DIEA. After washing with DMF, the DDE group was removed by treating the resin in a manual shaker 4×2 minutes with a solution of 2% anhydrous hydrazine in DMF. The resin was returned to the synthesizer and the final amino acids were coupled according to the above protocol.

The peptide resin (0.748 g) was simultaneously deprotected and cleaved from the resin with 10 ml of a mixture of TFA/phenol/ethanedithiol/thioanisole/water 10 ml/1.5 g/3 ml/0.5 ml/0.5 ml for 4 hr at ambient temperature. The resin was removed by filtration and the filtrate added to 200 ml of diethyl ether and stirred for hr. The resulting solid was isolated by centrifugation, washed well with ether and dried under reduced pressure to give 0.26 g of a white solid.

The crude material was injected in three equal aliquots onto two Vydac C-18 (25×250 mm, 100 columns in tandem and eluted using a 20-100% (80% acetonitrile/0.1% trifluoroacetic acid in water) over 120 min at a flow rate of 5 mL/min. Yields of the peptides were typically between 36-65 mg. The observed and calculated molecular weights were in good accordance. The characteristics of the synthesized alpha-MSH derivatives are shown in Table 2.

TABLE 2

| Formula | Molecular formula | MW (Da) observed |
|---|---|---|
| II | $C_{88}H_{141}N_{21}O_{26}S_2$ | 1,973.0 |
| III | $C_{85}H_{134}N_{22}O_{23}S_2$ | 1,896.9 |
| IV | $C_{78}H_{125}N_{21}O_{24}S_2$ | 1,805.8 |
| V | $C_{90}H_{144}N_{18}O_{23}S$ | 1,878.9 |
| VI | $C_{105}H_{166}N_{24}O_{32}$ | 2,277.0 |
| VII | $C_{105}H_{166}N_{24}O_{32}$ | 2,277.0 |
| VIII | $C_{106}H_{171}N_{25}O_{30}$ | 2,275.6 |
| IX | $C_{108}H_{173}N_{25}O_{31}$ | 2,318.2 |
| X | $C_{135}H_{226}N_{26}O_{44}$ | 2,917.7 |
| XI | $C_{77}H_{124}N_{18}O_{22}$ | 1,654.5 |
| XII | $C_{77}H_{124}N_{18}O_{23}$ | 1,670.6 |
| XIII | $C_{77}H_{124}N_{18}O_{22}$ | 1,654.7 |
| XIV | $C_{77}H_{124}N_{18}O_{23}$ | 1,670.6 |
| XV | $C_{77}H_{124}N_{18}O_{22}$ | 1,654.5 |

Peptide of Formulae XI-XV.

1.25 g of 0.20 meq/g NovaSyn TGR Novabiochem amide resin was used. The protecting groups used were N-terminal FMOC, His(Trt), Arg(Pmc), Tyr(BOC), Lys(BOC), Lys(Mtt) and Asp(O-Dmb). Deprotection was with piperidine, according to the FastMoc program. The residues were coupled to give, for example, FMOC-Asp(O-Dmb)-His(Trt), Phe-Lys(BOC)-Tyr(BOC)-Lys(Mtt)-Resin. The resin was treated manually with 1% TFA in methylene chloride for 20 minutes and then washed well with methylene chloride and NMP. The partially deprotected resis peptide was treated with HATU in a mixture of DMF and NMP for 30 min at ambient temperature to form the lactam. Following formation of the lactam the resin was returned to the synthesizer for the final couplings of FMOC-Nle, FMOC-PEG$_{12}$-CO$_2$H and BOC$_3$-hydrazinoacetic acid. The peptide resin (2.15 g) was simultaneously deprotected and cleaved from the resin with 10 ml of a mixture of TFA/phenol/ethanedithiol/thioanisole/water 10 ml/1.5 g/3 ml/0.5 ml/0.5 ml for 4 hr at ambient temperature. The resin was removed by filtration and the filtrate added to 400 ml of diethyl ether and stirred for hr. The resulting solid was isolated by centrifugation, washed well with ether and dried under reduced pressure to give 0.48 g of a white solid.

The crude material was injected in three equal aliquots onto two Vydac C-18 (25×250 mm, 100 columns in tandem and eluted using a 20-100% (80% acetonitrile/0.1% trifluoroacetic acid in water) over 120 min at a flow rate of 5 mL/min. Yields of the peptides were typically between 15-18 mg. The observed and calculated molecular weights were in good agreement.

Example 2

Preparation of Mono- or Di-Substituted Alpha-MSH Derivative-Fc Conjugates

Deglycosylation of 7E3 IgG Fc

7E3 IgG Fc is a Fc portion of an IgG prepared by papain digestion to generate abciximab (CAS registry number 143653-53-6) using standard methods. 135 ml of Fc (5 mg/ml) was dialyzed into 10 mM Tris, pH 7.5. 100 µl of PNGase F (500,000 u/ml) was added to the dialysate and the resulting solution incubated at 37° for 3 days. The deglycosylated Fc was purified on a TosoHaas phenyl 5PW column (5.5×200 mm, 10µ) eluted with the gradient of 0-50% buffer B at a flow rate of 11 ml/min (Buffer A: 0.1 M sodium phosphate, 1 M ammonium sulfate, pH 6.5; Buffer B: 0.1 M sodium phosphate, pH 6.5).

Molecular Weight Calcd: 49,864.4. Found: 49,868.4.

Oxidation of Deglycosylated Fc 55 ml of deglycosylated Fc (8.9 mg/ml) was dialyzed into 1% NaHCO$_3$, pH 8.4, to give 56.3 ml of 8.6 mg/ml. The concentration was adjusted to 5.1 mg/ml ($10^{-4}$ mmol of protein/ml, equivalent to $2\times10^{-4}$ mmol of N-terminal threonine/ml) by the addition of 40.6 ml of 1% NaHCO$_3$, pH 8.4. 11.9 ml of 12.5 mg/ml of methionine in 1% NaHCO$_3$, pH 8.4 was added to the Fc solution. 2.12 ml (42.4 mg) of 20 mg/ml NaIO$_4$ in water was added to the Fc. The reaction mixture was gently agitated at ambient temperature for 15 minutes. Ethylene glycol (2.8 g, 2.3 ml) was added and the reaction gently agitated for an additional 20 minutes. The solution was dialyzed into 0.1 M NaOAc, pH 4.5 to give 120 ml of 4.0 mg/ml. The solution was divided into 2.5 ml aliquots, frozen at −20° C. and used without further purification.

Preparation of Mono- and Di-Substituted Alpha-MSH Derivative-Fc Conjugates 0.5-10 mg of the peptides having Formulae II-XV were added into the Fc aldehyde (typically 3.0 ml, 2.68 mg/ml). The tube was stored at 4° C. overnight. 100 µl of 10 mg/ml of NaBH$_3$CN in water was added to the reaction mixture and the reaction was stored at 4° C. overnight. Following the addition of 100-200 mg of ammonium sulfate, the sample was injected onto a TosoHaas phenyl or ether 5PW column (21.5×150 mm, 10µ) and eluted with the 0-100% gradient (Buffer A=0.1 M sodium phosphate/1M ammonium sulfate, pH 6.5; Bufer B=0.1 M sodium phosphate/1M ammonium sulfate, pH 6.5) over 180 minutes, collecting 6 ml fractions.

Column fractions were analyzed with an Agilent Bioanalyzer 2100 using a Protein 80 Kit and processed according to the manufacturer's instructions. Fractions containing the desired product were pooled, concentrated using an Amicon Ultra-15 Centrifugal Filter Device with a 10 kDa molecular weight cut-off and dialyzed into PBS using a Pierce Slide-a-Lyzer dialysis cassette with a molecular weight cut-off of 10 kDa. Typical yields were 1.2-12 mg. The observed and calculated molecular weights were in good accordance. Table 3 shows the prepared alpha-MSH derivative-Fc conjugates.

TABLE 3

| Peptide Formula | Fc conjugate substitution | EC50 (nM) |
|---|---|---|
| II | mono | 12.04 |
|  | di | 1.83 |
| III | di | 13.24 |
| IV | mono | 8.54 |
|  | di | 6.21 |
| V | mono |  |
|  | di |  |
| V | di | 14.40 |
| VII | di | 5.70 |
| VIII | mono | 53.61 |
| IX | mono | 35.65 |
| X | di | 1.39 |
| XI | mono | 4.41 |
|  | di | 0.45 |
| XII | mono | 12.00 |
|  | di | 1.83 |
| XIII | mono | 13.20 |
|  | di | 13.20 |
| XIV | mono |  |
|  | di | 4.15 |
| XV | mono | 85.40 |
|  | di | 6.30 |

Example 3

Biological Activity of Mono- or Di-Substituted Alpha-MSH Derivative-Fc Conjugates Cyclic AMP (cAMP) Assay For the assay, CHO cells at density 65,000 cells per well were plated onto 96-well tissue culture treated plates 100 µl per well in DMEM/F12, 10% FBS, 1% Sodium Pyruvate, 1% L-Glutamine, and the plates were incubated overnight at 37° C. Next day, the media was aspirated off cell culture plates, replaced with 90 µL of warmed serum-free DMEM/F12 plus 1 mM IBMX (Sigma 17018) and incubated for 15 minutes at 37° C. 10 µL of serial dilutions (40 µM-4 nM) of each alpha-MSH derivative-Fc conjugate diluted in 0.5% BSA in PBS were added to the 90 µL of IBMX media and cells and stimulated for 15 minutes at 37° C. The stimulation media was aspirated off and replaced with 100 µL of lysis buffer provided in the kit (Tropix cAMP-Screen™ System Chemiluminescent Immunoassay System from Applera-Applied Biosystems) and incubated for 30 minutes at 37° C. Cell lysate or cAMP standard (60 µl/well) was added to the assay plate. The concentrations of cAMP standard were from 0.006 to 6000

µmol cAMP per 60 The cAMP-AP Conjugate was diluted 1:100 with Conjugate Dilution Buffer and 30 µl was added to each well of the provided anti-mouse antibody-coated plate in the Tropix kit followed by the addition of 60 ul/well of anti-cAMP antibody. The plates were incubated at ambient temperature for 60 minutes with gentle shaking and then washed plate 6 times (300 µl/well) with provided wash buffer. 100 µl/well of substrate/enhancer solution was added and the plate covered with foil, and incubated 30 minutes at ambient temperature with gentle shaking. The plates were read on a Victor³V 1420 Multilabel Counter (Perkin Elmer) using luminescence measurements.

$EC_{50}$ values for the tested alpha-MSH derivative-Fc conjugates are shown in Table 3. Acylated alpha-MSH (Phoenix Pharamceuticals), (Ac-NH-Ser-Tyr-Ser-Met-Glu-His-Phe-Arg-Trp-Gly-Lys-Pro-Val-CO-NH$_2$) (SEQ ID NO: 24) was used as a reference. The reference exhibited a sigmoidal dose-response curve with an $EC_{50}$ value of 0.1549 nM.

The alpha-MSH derivative-Fc conjugates mono-substituted Formula V-Fc, di-substituted Formula V-Fc, and mono-substituted Formula XIV-Fc conjugates were tested at a single dose of 0.26 µM in the cAMP assays. The conjugates stimulated cAMP levels an average of 35.663 µmol/well, 12.879 µmol/well, and 48.717 µmol/well, respectively.

Example 4

Selectivity of Mono- or Di-Substituted Alpha-MSH Derivative-Fc Conjugates

Receptor selectivity of conjugates formula X-Fc and formula VII-Fc were assayed using GeneBLAzer assay kits and CHO-K1 cell lines overexpressing MC1R (SEQ ID NO: 5), MC3R (SEQ ID NO: 6), MC4R (SEQ ID NO: 7), or MC5R (SEQ ID NO: 8) (Invitrogen, Carlsbad, Calif.) according to manufacturer's instruction. Increase in the cAMP upon receptor activation was assessed using a beta-lactamase reporter gene under control of the Cyclic AMP Response Element (CRE). EC50 values for the assays are shown in Table 4.

TABLE 4

| Conjugate | $EC_{50}$ (nM) | | | |
| --- | --- | --- | --- | --- |
| | MC1R | MC3R | MC4R | MC5R |
| Formula VII-Fc | 48.4 | 2.9 | 2.4 | 9.6 |
| Formula X-Fc | 3.9 | 30.9 | 34 | 968.7 |

The invention claimed is:

1. An alpha-MSH derivative-Fc conjugate, wherein the alpha-MSH derivative has a structure shown in Formula X (SEQ ID NO: 18), and the alpha-MSH derivative is coupled to the Fc via a hydrazine linker.

2. The alpha-MSH derivative-Fc conjugate of claim 1, wherein the Fc is derived from an IgG1 Fc of SEQ ID NO: 2 or an IgG4 Fc of SEQ ID NO: 3.

3. A pharmaceutical composition comprising the alpha-MSH derivative-Fc conjugate of claim 1 in combination with a pharmaceutically acceptable carrier.

* * * * *

SEQUENCE LISTING

<160> NUMBER OF SEQ ID NOS: 24

<210> SEQ ID NO 1
<211> LENGTH: 13
<212> TYPE: PRT
<213> ORGANISM: Homo sapiens

<400> SEQUENCE: 1

Ser Tyr Ser Met Glu His Phe Arg Trp Gly Lys Pro Val
1               5                   10

<210> SEQ ID NO 2
<211> LENGTH: 330
<212> TYPE: PRT
<213> ORGANISM: Homo sapiens

<400> SEQUENCE: 2

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

```
Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 3
<211> LENGTH: 330
<212> TYPE: PRT
<213> ORGANISM: Homo sapiens

<400> SEQUENCE: 3

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190
```

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 4
<211> LENGTH: 9
<212> TYPE: PRT
<213> ORGANISM: Artififial sequence
<220> FEATURE:
<223> OTHER INFORMATION: Portion of a human IgG variable region

<400> SEQUENCE: 4

Gly Thr Leu Val Thr Leu Val Ser Ser
1               5

<210> SEQ ID NO 5
<211> LENGTH: 317
<212> TYPE: PRT
<213> ORGANISM: Homo sapiens

<400> SEQUENCE: 5

Met Ala Val Gln Gly Ser Gln Arg Arg Leu Leu Gly Ser Leu Asn Ser
1               5                   10                  15

Thr Pro Thr Ala Ile Pro Gln Leu Gly Leu Ala Ala Asn Gln Thr Gly
            20                  25                  30

Ala Arg Cys Leu Glu Val Ser Ile Ser Asp Gly Leu Phe Leu Ser Leu
        35                  40                  45

Gly Leu Val Ser Leu Val Glu Asn Ala Leu Val Val Ala Thr Ile Ala
    50                  55                  60

Lys Asn Arg Asn Leu His Ser Pro Met Tyr Cys Phe Ile Cys Cys Leu
65                  70                  75                  80

Ala Leu Ser Asp Leu Leu Val Ser Gly Ser Asn Val Leu Glu Thr Ala
                85                  90                  95

Val Ile Leu Leu Leu Glu Ala Gly Ala Leu Val Ala Arg Ala Ala Val
            100                 105                 110

Leu Gln Gln Leu Asp Asn Val Ile Asp Val Ile Thr Cys Ser Ser Met
        115                 120                 125

Leu Ser Ser Leu Cys Phe Leu Gly Ala Ile Ala Val Asp Arg Tyr Ile
    130                 135                 140

Ser Ile Phe Tyr Ala Leu Arg Tyr His Ser Ile Val Thr Leu Pro Arg
145                 150                 155                 160

Ala Arg Arg Ala Val Ala Ala Ile Trp Val Ala Ser Val Val Phe Ser

```
                    165                 170                 175
Thr Leu Phe Ile Ala Tyr Tyr Asp His Val Ala Val Leu Leu Cys Leu
            180                 185                 190

Val Val Phe Phe Leu Ala Met Leu Val Leu Met Ala Val Leu Tyr Val
        195                 200                 205

His Met Leu Ala Arg Ala Cys Gln His Ala Gln Gly Ile Ala Arg Leu
    210                 215                 220

His Lys Arg Gln Arg Pro Val His Gln Gly Phe Gly Leu Lys Gly Ala
225                 230                 235                 240

Val Thr Leu Thr Ile Leu Leu Gly Ile Phe Phe Leu Cys Trp Gly Pro
                245                 250                 255

Phe Phe Leu His Leu Thr Leu Ile Val Leu Cys Pro Glu His Pro Thr
            260                 265                 270

Cys Gly Cys Ile Phe Lys Asn Phe Asn Leu Phe Leu Ala Leu Ile Ile
        275                 280                 285

Cys Asn Ala Ile Ile Asp Pro Leu Ile Tyr Ala Phe His Ser Gln Glu
    290                 295                 300

Leu Arg Arg Thr Leu Lys Glu Val Leu Thr Cys Ser Trp
305                 310                 315

<210> SEQ ID NO 6
<211> LENGTH: 323
<212> TYPE: PRT
<213> ORGANISM: Homo sapiens

<400> SEQUENCE: 6

Met Asn Ala Ser Cys Cys Leu Pro Ser Val Gln Pro Thr Leu Pro Asn
 1               5                  10                  15

Gly Ser Glu His Leu Gln Ala Pro Phe Phe Ser Asn Gln Ser Ser Ser
                20                  25                  30

Ala Phe Cys Glu Gln Val Phe Ile Lys Pro Glu Val Phe Leu Ser Leu
            35                  40                  45

Gly Ile Val Ser Leu Leu Glu Asn Ile Leu Val Ile Leu Ala Val Val
        50                  55                  60

Arg Asn Gly Asn Leu His Ser Pro Met Tyr Phe Phe Leu Cys Ser Leu
65                  70                  75                  80

Ala Val Ala Asp Met Leu Val Ser Val Ser Asn Ala Leu Glu Thr Ile
                85                  90                  95

Met Ile Ala Ile Val His Ser Asp Tyr Leu Thr Phe Glu Asp Gln Phe
            100                 105                 110

Ile Gln His Met Asp Asn Ile Phe Asp Ser Met Ile Cys Ile Ser Leu
        115                 120                 125

Val Ala Ser Ile Cys Asn Leu Leu Ala Ile Ala Val Asp Arg Tyr Val
    130                 135                 140

Thr Ile Phe Tyr Ala Leu Arg Tyr His Ser Ile Met Thr Val Arg Lys
145                 150                 155                 160

Ala Leu Thr Leu Ile Val Ala Ile Trp Val Cys Cys Gly Val Cys Gly
                165                 170                 175

Val Val Phe Ile Val Tyr Ser Glu Ser Lys Met Val Ile Val Cys Leu
            180                 185                 190

Ile Thr Met Phe Phe Ala Met Met Leu Leu Met Gly Thr Leu Tyr Val
        195                 200                 205

His Met Phe Leu Phe Ala Arg Leu His Val Lys Arg Ile Ala Ala Leu
    210                 215                 220

Pro Pro Ala Asp Gly Val Ala Pro Gln Gln His Ser Cys Met Lys Gly
```

```
                    225                 230                 235                 240
Ala Val Thr Ile Thr Ile Leu Leu Gly Val Phe Ile Phe Cys Trp Ala
                245                 250                 255

Pro Phe Phe Leu His Leu Val Leu Ile Ile Thr Cys Pro Thr Asn Pro
                260                 265                 270

Tyr Cys Ile Cys Tyr Thr Ala His Phe Asn Thr Tyr Leu Val Leu Ile
                275                 280                 285

Met Cys Asn Ser Val Ile Asp Pro Leu Ile Tyr Ala Phe Arg Ser Leu
                290                 295                 300

Glu Leu Arg Asn Thr Phe Arg Glu Ile Leu Cys Gly Cys Asn Gly Met
305                 310                 315                 320

Asn Leu Gly

<210> SEQ ID NO 7
<211> LENGTH: 332
<212> TYPE: PRT
<213> ORGANISM: Homo sapiens

<400> SEQUENCE: 7

Met Val Asn Ser Thr His Arg Gly Met His Thr Ser Leu His Leu Trp
  1               5                  10                  15

Asn Arg Ser Ser Tyr Arg Leu His Ser Asn Ala Ser Glu Ser Leu Gly
                20                  25                  30

Lys Gly Tyr Ser Asp Gly Gly Cys Tyr Glu Gln Leu Phe Val Ser Pro
            35                  40                  45

Glu Val Phe Val Thr Leu Gly Val Ile Ser Leu Leu Glu Asn Ile Leu
        50                  55                  60

Val Ile Val Ala Ile Ala Lys Asn Lys Asn Leu His Ser Pro Met Tyr
 65                  70                  75                  80

Phe Phe Ile Cys Ser Leu Ala Val Ala Asp Met Leu Val Ser Val Ser
                85                  90                  95

Asn Gly Ser Glu Thr Ile Val Ile Thr Leu Leu Asn Ser Thr Asp Thr
            100                 105                 110

Asp Ala Gln Ser Phe Thr Val Asn Ile Asp Asn Val Ile Asp Ser Val
        115                 120                 125

Ile Cys Ser Ser Leu Leu Ala Ser Ile Cys Ser Leu Leu Ser Ile Ala
130                 135                 140

Val Asp Arg Tyr Phe Thr Ile Phe Tyr Ala Leu Gln Tyr His Asn Ile
145                 150                 155                 160

Met Thr Val Lys Arg Val Gly Ile Ile Ile Ser Cys Ile Trp Ala Ala
                165                 170                 175

Cys Thr Val Ser Gly Ile Leu Phe Ile Ile Tyr Ser Asp Ser Ser Ala
            180                 185                 190

Val Ile Ile Cys Leu Ile Thr Met Phe Phe Thr Met Leu Ala Leu Met
        195                 200                 205

Ala Ser Leu Tyr Val His Met Phe Leu Met Ala Arg Leu His Ile Lys
210                 215                 220

Arg Ile Ala Val Leu Pro Gly Thr Gly Ala Ile Arg Gln Gly Ala Asn
225                 230                 235                 240

Met Lys Gly Ala Ile Thr Leu Thr Ile Leu Ile Gly Val Phe Val Val
                245                 250                 255

Cys Trp Ala Pro Phe Phe Leu His Leu Ile Phe Tyr Ile Ser Cys Pro
            260                 265                 270

Gln Asn Pro Tyr Cys Val Cys Phe Met Ser His Phe Asn Leu Tyr Leu
        275                 280                 285
```

```
Ile Leu Ile Met Cys Asn Ser Ile Ile Asp Pro Leu Ile Tyr Ala Leu
    290                 295                 300

Arg Ser Gln Glu Leu Arg Lys Thr Phe Lys Glu Ile Ile Cys Cys Tyr
305                 310                 315                 320

Pro Leu Gly Gly Leu Cys Asp Leu Ser Ser Arg Tyr
            325                 330

<210> SEQ ID NO 8
<211> LENGTH: 325
<212> TYPE: PRT
<213> ORGANISM: Homo sapiens

<400> SEQUENCE: 8

Met Asn Ser Ser Phe His Leu His Phe Asp Leu Asn Leu Asn Ala
1               5                   10                  15

Thr Glu Gly Asn Leu Ser Gly Pro Asn Val Lys Asn Lys Ser Ser Pro
                20                  25                  30

Cys Glu Asp Met Gly Ile Ala Val Glu Val Phe Leu Thr Leu Gly Val
            35                  40                  45

Ile Ser Leu Leu Glu Asn Ile Leu Val Ile Gly Ala Ile Val Lys Asn
50                  55                  60

Lys Asn Leu His Ser Pro Met Tyr Phe Phe Val Cys Ser Leu Ala Val
65                  70                  75                  80

Ala Asp Met Leu Val Ser Met Ser Ser Ala Trp Glu Thr Ile Thr Ile
                85                  90                  95

Tyr Leu Leu Asn Asn Lys His Leu Val Ile Ala Asp Ala Phe Val Arg
                100                 105                 110

His Ile Asp Asn Val Phe Asp Ser Met Ile Cys Ile Ser Val Val Ala
            115                 120                 125

Ser Met Cys Ser Leu Leu Ala Ile Ala Val Asp Arg Tyr Val Thr Ile
130                 135                 140

Phe Tyr Ala Leu Arg Tyr His His Ile Met Thr Ala Arg Arg Ser Gly
145                 150                 155                 160

Ala Ile Ile Ala Gly Ile Trp Ala Phe Cys Thr Gly Cys Gly Ile Val
                165                 170                 175

Phe Ile Leu Tyr Ser Glu Ser Thr Tyr Val Ile Leu Cys Leu Ile Ser
                180                 185                 190

Met Phe Phe Ala Met Leu Phe Leu Leu Val Ser Leu Tyr Ile His Met
            195                 200                 205

Phe Leu Leu Ala Arg Thr His Val Lys Arg Ile Ala Ala Leu Pro Gly
210                 215                 220

Ala Ser Ser Ala Arg Gln Arg Thr Ser Met Gln Gly Ala Val Thr Val
225                 230                 235                 240

Thr Met Leu Leu Gly Val Phe Thr Val Cys Trp Ala Pro Phe Phe Leu
                245                 250                 255

His Leu Thr Leu Met Leu Ser Cys Pro Gln Asn Leu Tyr Cys Ser Arg
                260                 265                 270

Phe Met Ser His Phe Asn Met Tyr Leu Ile Leu Ile Met Cys Asn Ser
            275                 280                 285

Val Met Asp Pro Leu Ile Tyr Ala Phe Arg Ser Gln Glu Met Arg Lys
290                 295                 300

Thr Phe Lys Glu Ile Ile Cys Cys Arg Gly Phe Arg Ile Ala Cys Ser
305                 310                 315                 320

Phe Pro Arg Arg Asp
                325
```

<210> SEQ ID NO 9
<211> LENGTH: 297
<212> TYPE: PRT
<213> ORGANISM: Homo sapiens

<400> SEQUENCE: 9

```
Met Lys His Ile Ile Asn Ser Tyr Glu Asn Ile Asn Asn Thr Ala Arg
 1               5                  10                  15

Asn Asn Ser Asp Cys Pro Arg Val Val Leu Pro Glu Glu Ile Phe Phe
            20                  25                  30

Thr Ile Ser Ile Val Gly Val Leu Glu Asn Leu Ile Val Leu Leu Ala
        35                  40                  45

Val Phe Lys Asn Lys Asn Leu Gln Ala Pro Met Tyr Phe Phe Ile Cys
 50                  55                  60

Ser Leu Ala Ile Ser Asp Met Leu Gly Ser Leu Tyr Lys Ile Leu Glu
 65                  70                  75                  80

Asn Ile Leu Ile Ile Leu Arg Asn Met Gly Tyr Leu Lys Pro Arg Gly
                85                  90                  95

Ser Phe Glu Thr Thr Ala Asp Asp Ile Ile Asp Ser Leu Phe Val Leu
            100                 105                 110

Ser Leu Leu Gly Ser Ile Phe Ser Leu Ser Val Ile Ala Ala Asp Arg
        115                 120                 125

Tyr Ile Thr Ile Phe His Ala Leu Arg Tyr His Ser Ile Val Thr Met
130                 135                 140

Arg Arg Thr Val Val Val Leu Thr Val Ile Trp Thr Phe Cys Thr Gly
145                 150                 155                 160

Thr Gly Ile Thr Met Val Ile Phe Ser His His Val Pro Thr Val Ile
                165                 170                 175

Thr Phe Thr Ser Leu Phe Pro Leu Met Leu Val Phe Ile Leu Cys Leu
            180                 185                 190

Tyr Val His Met Phe Leu Leu Ala Arg Ser His Thr Arg Lys Ile Ser
        195                 200                 205

Thr Leu Pro Arg Ala Asn Met Lys Gly Ala Ile Thr Leu Thr Ile Leu
    210                 215                 220

Leu Gly Val Phe Ile Phe Cys Trp Ala Pro Phe Val Leu His Val Leu
225                 230                 235                 240

Leu Met Thr Phe Cys Pro Ser Asn Pro Tyr Cys Ala Cys Tyr Met Ser
                245                 250                 255

Leu Phe Gln Val Asn Gly Met Leu Ile Met Cys Asn Ala Val Ile Asp
            260                 265                 270

Pro Phe Ile Tyr Ala Phe Arg Ser Pro Glu Leu Arg Asp Ala Phe Lys
        275                 280                 285

Lys Met Ile Phe Cys Ser Arg Tyr Trp
290                 295
```

<210> SEQ ID NO 10
<211> LENGTH: 10
<212> TYPE: PRT
<213> ORGANISM: Artificial Sequence
<220> FEATURE:
<223> OTHER INFORMATION: aMSH derivative
<220> FEATURE:
<221> NAME/KEY: MOD_RES
<222> LOCATION: (1)...(1)
<223> OTHER INFORMATION: 3-[2-(2-{2-[2-(2-[2-{2-[2-(2-{2-[2-(2-Amino-
      ethoxy)-ethoxy]-ethoxy}-ethoxy)-ethoxy]-ethoxy}-ethoxy]-
      ethoxy]-ethoxy}-ethoxy)-ethoxy]-propionic
      acid

```
<220> FEATURE:
<221> NAME/KEY: VARIANT
<222> LOCATION: (4)...(4)
<223> OTHER INFORMATION: Xaa4 is D-Phenylalanine
<220> FEATURE:
<221> NAME/KEY: DISULFID
<222> LOCATION: (1)...(7)
<223> OTHER INFORMATION: cyclo cys1:cys7
<220> FEATURE:
<221> NAME/KEY: AMIDATION
<222> LOCATION: (10)...(10)

<400> SEQUENCE: 10

Cys Glu His Xaa Arg Trp Cys Lys Pro Val
1               5                   10

<210> SEQ ID NO 11
<211> LENGTH: 9
<212> TYPE: PRT
<213> ORGANISM: Artificial Sequence
<220> FEATURE:
<223> OTHER INFORMATION: aMSH derivative
<220> FEATURE:
<221> NAME/KEY: VARIANT
<222> LOCATION: (2)...(2)
<223> OTHER INFORMATION: Xaa2 Nle
<220> FEATURE:
<221> NAME/KEY: VARIANT
<222> LOCATION: (5)...(5)
<223> OTHER INFORMATION: Xaa5  is 2-D-Nal
<220> FEATURE:
<221> NAME/KEY: AMIDATION
<222> LOCATION: (9)...(9)
<220> FEATURE:
<221> NAME/KEY: DISULFID
<222> LOCATION: (1)...(9)
<223> OTHER INFORMATION: cyclo cys1:cys9
<220> FEATURE:
<221> NAME/KEY: MOD_RES
<222> LOCATION: (1)...(1)
<223> OTHER INFORMATION: 3-[2-(2-{2-[2-(2-[2-{2-[2-(2-{2-[2-(2-Amino-
      ethoxy)-ethoxy]-ethoxy}-ethoxy)-ethoxy]-ethoxy}-ethoxy]-
      ethoxy)-ethoxy]-ethoxy}-ethoxy)-ethoxy]-propionic
      acid

<400> SEQUENCE: 11

Cys Xaa Arg His Xaa Arg Trp Gly Cys
1               5

<210> SEQ ID NO 12
<211> LENGTH: 8
<212> TYPE: PRT
<213> ORGANISM: Artificial Sequence
<220> FEATURE:
<223> OTHER INFORMATION: aMSH derivative
<220> FEATURE:
<221> NAME/KEY: MOD_RES
<222> LOCATION: (1)...(1)
<223> OTHER INFORMATION: 3-[2-(2-{2-[2-(2-[2-{2-[2-(2-{2-[2-(2-Amino-
      ethoxy)-ethoxy]-ethoxy}-ethoxy)-ethoxy]-ethoxy}-ethoxy]-
      ethoxy)-ethoxy]-ethoxy}-ethoxy)-ethoxy]-propionic
      acid
<220> FEATURE:
<221> NAME/KEY: VARIANT
<222> LOCATION: (1)...(1)
<223> OTHER INFORMATION: Xaa1 is D-Arginine
<220> FEATURE:
<221> NAME/KEY: VARIANT
<222> LOCATION: (5)...(5)
<223> OTHER INFORMATION: Xaa5 is  D-Phenylalanine
<220> FEATURE:
<221> NAME/KEY: AMIDATION
<222> LOCATION: (8)...(8)
<220> FEATURE:
<221> NAME/KEY: DISULFID
<222> LOCATION: (2)...(8)
```

```
<223> OTHER INFORMATION: cyclo cys2:cys8

<400> SEQUENCE: 12

Xaa Cys Glu His Xaa Arg Trp Cys
 1               5

<210> SEQ ID NO 13
<211> LENGTH: 9
<212> TYPE: PRT
<213> ORGANISM: Artificial Sequence
<220> FEATURE:
<223> OTHER INFORMATION: aMSH derivative
<220> FEATURE:
<221> NAME/KEY: MOD_RES
<222> LOCATION: (1)...(1)
<223> OTHER INFORMATION: 3-[2-(2-{2-[2-(2-[2-{2-[2-(2-{2-[2-(2-Amino-
      ethoxy)-ethoxy]-ethoxy}-ethoxy)-ethoxy]-ethoxy}-ethoxy]-
      ethoxy)-ethoxy]-ethoxy}-ethoxy)-ethoxy]-propionic
      acid
<220> FEATURE:
<221> NAME/KEY: VARIANT
<222> LOCATION: (3)...(3)
<223> OTHER INFORMATION: Xaa3 is D-Phenylalanine
<220> FEATURE:
<221> NAME/KEY: VARIANT
<222> LOCATION: (5)...(5)
<223> OTHER INFORMATION: Xaa5 is D-Tryptophan
<220> FEATURE:
<221> NAME/KEY: AMIDATION
<222> LOCATION: (9)...(9)

<400> SEQUENCE: 13

Met Pro Xaa Arg Xaa Phe Lys Pro Val
 1               5

<210> SEQ ID NO 14
<211> LENGTH: 13
<212> TYPE: PRT
<213> ORGANISM: Artificial Sequence
<220> FEATURE:
<223> OTHER INFORMATION: aMSH derivative
<220> FEATURE:
<221> NAME/KEY: MOD_RES
<222> LOCATION: (1)...(1)
<223> OTHER INFORMATION: 3-[2-(2-{2-[2-(2-[2-{2-[2-(2-{2-[2-(2-Amino-
      ethoxy)-ethoxy]-ethoxy}-ethoxy)-ethoxy]-ethoxy}-ethoxy]-
      ethoxy)-ethoxy]-ethoxy}-ethoxy)-ethoxy]-propionic
      acid
<220> FEATURE:
<221> NAME/KEY: VARIANT
<222> LOCATION: (4)...(4)
<223> OTHER INFORMATION: Xaa4 is Nle
<220> FEATURE:
<221> NAME/KEY: VARIANT
<222> LOCATION: (7)...(7)
<223> OTHER INFORMATION: Xaa7 is D-Phenylalanine
<220> FEATURE:
<221> NAME/KEY: AMIDATION
<222> LOCATION: (13)...(13)

<400> SEQUENCE: 14

Ser Tyr Ser Xaa Glu His Xaa Arg Trp Gly Lys Pro Val
 1               5                   10

<210> SEQ ID NO 15
<211> LENGTH: 13
<212> TYPE: PRT
<213> ORGANISM: Artificial Sequence
<220> FEATURE:
<223> OTHER INFORMATION: aMSH derivative
<220> FEATURE:
<221> NAME/KEY: MOD_RES
<222> LOCATION: (1)...(1)
<223> OTHER INFORMATION: 3-[2-(2-{2-[2-(2-[2-{2-[2-(2-{2-[2-(2-Amino-
```

```
        ethoxy)-ethoxy]-ethoxy}-ethoxy)-ethoxy-ethoxy}-ethoxy-
        ethoxy)-ethoxy]-ethoxy}-ethoxy)-ethoxy]-propionic
        acid
<220> FEATURE:
<221> NAME/KEY: VARIANT
<222> LOCATION: (4)...(4)
<223> OTHER INFORMATION: Xaa4 is Nle
<220> FEATURE:
<221> NAME/KEY: AMIDATION
<222> LOCATION: (13)...(13)

<400> SEQUENCE: 15

Ser Tyr Ser Xaa Glu His Phe Arg Trp Gly Lys Pro Val
 1               5                   10

<210> SEQ ID NO 16
<211> LENGTH: 13
<212> TYPE: PRT
<213> ORGANISM: Artificial Sequence
<220> FEATURE:
<223> OTHER INFORMATION: aMSH derivative
<220> FEATURE:
<221> NAME/KEY: VARIANT
<222> LOCATION: (4)...(4)
<223> OTHER INFORMATION: Xaa4 is Nle
<220> FEATURE:
<221> NAME/KEY: MOD_RES
<222> LOCATION: (5)...(5)
<223> OTHER INFORMATION: 3-[2-(2-{2-[2-(2-[2-{2-[2-(2-{2-[2-(2-Amino-
        ethoxy)-ethoxy]-ethoxy}-ethoxy)-ethoxy]-ethoxy}-ethoxy-
        ethoxy)-ethoxy]-ethoxy}-ethoxy)-ethoxy]-propionic
        acid
<220> FEATURE:
<221> NAME/KEY: AMIDATION
<222> LOCATION: (13)...(13)

<400> SEQUENCE: 16

Ser Tyr Ser Xaa Lys His Phe Arg Trp Gly Lys Pro Val
 1               5                   10

<210> SEQ ID NO 17
<211> LENGTH: 13
<212> TYPE: PRT
<213> ORGANISM: Artificial Sequence
<220> FEATURE:
<223> OTHER INFORMATION: aMSH derivative
<220> FEATURE:
<221> NAME/KEY: ACETYLATION
<222> LOCATION: (1)...(1)
<220> FEATURE:
<221> NAME/KEY: VARIANT
<222> LOCATION: (4)...(4)
<223> OTHER INFORMATION: Xaa4 is Nle
<220> FEATURE:
<221> NAME/KEY: MOD_RES
<222> LOCATION: (5)...(5)
<223> OTHER INFORMATION: 3-[2-(2-{2-[2-(2-[2-{2-[2-(2-{2-[2-(2-Amino-
        ethoxy)-ethoxy]-ethoxy}-ethoxy)-ethoxy]-ethoxy}-ethoxy-
        ethoxy)-ethoxy]-ethoxy}-ethoxy)-ethoxy]-propionic
        acid
<220> FEATURE:
<221> NAME/KEY: AMIDATION
<222> LOCATION: (13)...(13)

<400> SEQUENCE: 17

Ser Tyr Ser Xaa Lys His Phe Arg Trp Gly Lys Pro Val
 1               5                   10

<210> SEQ ID NO 18
<211> LENGTH: 13
<212> TYPE: PRT
<213> ORGANISM: Artificial Sequence
<220> FEATURE:
<223> OTHER INFORMATION: aMSH derivative
```

```
<220> FEATURE:
<221> NAME/KEY: ACETYLATION
<222> LOCATION: (1)...(1)
<220> FEATURE:
<221> NAME/KEY: VARIANT
<222> LOCATION: (4)...(4)
<223> OTHER INFORMATION: Xaa4 is Nle
<220> FEATURE:
<221> NAME/KEY: MOD_RES
<222> LOCATION: (5)...(5)
<223> OTHER INFORMATION: 3-[2-(2-{2-[2-(2-[2-{2-[2-(2-{2-[2-(2-Amino-
      ethoxy)-ethoxy]-ethoxy}-ethoxy)-ethoxy]-ethoxy}-ethoxy-
      ethoxy)-ethoxy]-ethoxy}-ethoxy)-ethoxy]-propionic
      acid
<220> FEATURE:
<221> NAME/KEY: VARIANT
<222> LOCATION: (7)...(7)
<223> OTHER INFORMATION: Xaa7 is D-Phenylalanine
<220> FEATURE:
<221> NAME/KEY: AMIDATION
<222> LOCATION: (13)...(13)

<400> SEQUENCE: 18

Ser Tyr Ser Xaa Lys His Xaa Arg Trp Gly Lys Pro Val
 1               5                  10

<210> SEQ ID NO 19
<211> LENGTH: 7
<212> TYPE: PRT
<213> ORGANISM: Artificial Sequence
<220> FEATURE:
<223> OTHER INFORMATION: aMSH derivative
<220> FEATURE:
<221> NAME/KEY: VARIANT
<222> LOCATION: (1)...(1)
<223> OTHER INFORMATION: Xaa1 is Nle
<220> FEATURE:
<221> NAME/KEY: MOD_RES
<222> LOCATION: (1)...(1)
<223> OTHER INFORMATION: 3-[2-(2-{2-[2-(2-[2-{2-[2-(2-{2-[2-(2-Amino-
      ethoxy)-ethoxy]-ethoxy}-ethoxy)-ethoxy]-ethoxy}-ethoxy-
      ethoxy)-ethoxy]-ethoxy}-ethoxy)-ethoxy]-propionic
      acid
<220> FEATURE:
<221> NAME/KEY: VARIANT
<222> LOCATION: (4)...(4)
<223> OTHER INFORMATION: Xaa4 is D-Phenylalanine
<220> FEATURE:
<221> NAME/KEY: MOD_RES
<222> LOCATION: (2)...(7)
<223> OTHER INFORMATION: cyclo Asp2:Lys7
<220> FEATURE:
<221> NAME/KEY: AMIDATION
<222> LOCATION: (7)...(7)

<400> SEQUENCE: 19

Xaa Asp His Xaa Arg Trp Lys
 1               5

<210> SEQ ID NO 20
<211> LENGTH: 7
<212> TYPE: PRT
<213> ORGANISM: Artificial Sequence
<220> FEATURE:
<223> OTHER INFORMATION: aMSH derivative
<220> FEATURE:
<221> NAME/KEY: VARIANT
<222> LOCATION: (1)...(1)
<223> OTHER INFORMATION: Xaa1 is Nle
<220> FEATURE:
<221> NAME/KEY: MOD_RES
<222> LOCATION: (1)...(1)
<223> OTHER INFORMATION: 3-[2-(2-{2-[2-(2-[2-{2-[2-(2-{2-[2-(2-Amino-
      ethoxy)-ethoxy]-ethoxy}-ethoxy)-ethoxy]-ethoxy}-ethoxy-
      ethoxy)-ethoxy]-ethoxy}-ethoxy)-ethoxy]-propionic
      acid
```

```
<220> FEATURE:
<221> NAME/KEY: VARIANT
<222> LOCATION: (4)...(4)
<223> OTHER INFORMATION: Xaa4 is D-Tyrosine
<220> FEATURE:
<221> NAME/KEY: MOD_RES
<222> LOCATION: (2)...(7)
<223> OTHER INFORMATION: cyclo Asp2:Lys7
<220> FEATURE:
<221> NAME/KEY: AMIDATION
<222> LOCATION: (7)...(7)

<400> SEQUENCE: 20

Xaa Asp His Xaa Arg Trp Lys
 1               5

<210> SEQ ID NO 21
<211> LENGTH: 7
<212> TYPE: PRT
<213> ORGANISM: Artificial Sequence
<220> FEATURE:
<223> OTHER INFORMATION: aMSH derivative
<220> FEATURE:
<221> NAME/KEY: VARIANT
<222> LOCATION: (1)...(1)
<223> OTHER INFORMATION: Xaa1 is Nle
<220> FEATURE:
<221> NAME/KEY: MOD_RES
<222> LOCATION: (1)...(1)
<223> OTHER INFORMATION: 3-[2-(2-{2-[2-(2-[2-{2-[2-(2-{2-[2-(2-Amino-
      ethoxy)-ethoxy]-ethoxy}-ethoxy)-ethoxy]-ethoxy}-ethoxy]-
      ethoxy)-ethoxy]-ethoxy}-ethoxy)-ethoxy]-propionic
      acid
<220> FEATURE:
<221> NAME/KEY: AMIDATION
<222> LOCATION: (7)...(7)
<220> FEATURE:
<221> NAME/KEY: MOD_RES
<222> LOCATION: (2)...(7)
<223> OTHER INFORMATION: cyclo Asp2:Lys7

<400> SEQUENCE: 21

Xaa Asp His Phe Arg Trp Lys
 1               5

<210> SEQ ID NO 22
<211> LENGTH: 7
<212> TYPE: PRT
<213> ORGANISM: Artificial Sequence
<220> FEATURE:
<223> OTHER INFORMATION: aMSH derivative
<220> FEATURE:
<221> NAME/KEY: VARIANT
<222> LOCATION: (1)...(1)
<223> OTHER INFORMATION: Xaa1 is Nle
<220> FEATURE:
<221> NAME/KEY: MOD_RES
<222> LOCATION: (1)...(1)
<223> OTHER INFORMATION: 3-[2-(2-{2-[2-(2-[2-{2-[2-(2-{2-[2-(2-Amino-
      ethoxy)-ethoxy]-ethoxy}-ethoxy)-ethoxy]-ethoxy}-ethoxy]-
      ethoxy)-ethoxy]-ethoxy}-ethoxy)-ethoxy]-propionic
      acid
<220> FEATURE:
<221> NAME/KEY: VARIANT
<222> LOCATION: (4)...(4)
<223> OTHER INFORMATION: Xaa4 is D-Tyrosine
<220> FEATURE:
<221> NAME/KEY: AMIDATION
<222> LOCATION: (7)...(7)
<220> FEATURE:
<221> NAME/KEY: MOD_RES
<222> LOCATION: (2)...(7)
<223> OTHER INFORMATION: Cyclo Asp2:Lys7

<400> SEQUENCE: 22
```

```
Xaa Asp His Xaa Lys Trp Lys
1               5

<210> SEQ ID NO 23
<211> LENGTH: 7
<212> TYPE: PRT
<213> ORGANISM: Artificial Sequence
<220> FEATURE:
<223> OTHER INFORMATION: aMSH derivative
<220> FEATURE:
<221> NAME/KEY: VARIANT
<222> LOCATION: (1)...(1)
<223> OTHER INFORMATION: Xaa1 is Nle
<220> FEATURE:
<221> NAME/KEY: MOD_RES
<222> LOCATION: (1)...(1)
<223> OTHER INFORMATION: 3-[2-(2-{2-[2-(2-[2-{2-[2-(2-{2-[2-(2-Amino-
      ethoxy)-ethoxy]-ethoxy}-ethoxy)-ethoxy]-ethoxy}-ethoxy]-
      ethoxy)-ethoxy]-ethoxy}-ethoxy)-ethoxy]-propionic
      acid
<220> FEATURE:
<221> NAME/KEY: AMIDATION
<222> LOCATION: (7)...(7)
<220> FEATURE:
<221> NAME/KEY: MOD_RES
<222> LOCATION: (2)...(7)
<223> OTHER INFORMATION: Cyclo Asp2:Lys7

<400> SEQUENCE: 23

Xaa Asp His Phe Lys Trp Lys
1               5

<210> SEQ ID NO 24
<211> LENGTH: 13
<212> TYPE: PRT
<213> ORGANISM: Homo Sapiens
<220> FEATURE:
<221> NAME/KEY: ACETYLATION
<222> LOCATION: (1)...(1)
<220> FEATURE:
<221> NAME/KEY: AMIDATION
<222> LOCATION: (13)...(13)

<400> SEQUENCE: 24

Ser Tyr Ser Met Glu His Phe Arg Trp Gly Lys Pro Val
1               5                   10
```